United States Patent
Mitsui et al.

(10) Patent No.: US 7,060,781 B2
(45) Date of Patent: Jun. 13, 2006

(54) 2,6-DIMETHYPHENOL COMPOSITION

(75) Inventors: Akira Mitsui, Chiba (JP); Osamu Shoji, Chiba (JP); Hitoshi Ota, Kanagawa (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 10/485,963

(22) PCT Filed: Aug. 6, 2002

(86) PCT No.: PCT/JP02/08030

§ 371 (c)(1),
(2), (4) Date: Feb. 6, 2004

(87) PCT Pub. No.: WO03/014050

PCT Pub. Date: Feb. 20, 2003

(65) Prior Publication Data

US 2004/0236060 A1    Nov. 25, 2004

(30) Foreign Application Priority Data

Aug. 7, 2001 (JP) .............................. 2001-239820

(51) Int. Cl.
  *C08G 65/38* (2006.01)
  *C08G 65/44* (2006.01)
(52) U.S. Cl. ....................... 528/217; 528/212; 528/214; 528/215; 528/397; 502/165

(58) Field of Classification Search ................ 528/217, 528/212, 214, 215, 397; 502/165
See application file for complete search history.

(56) References Cited

U.S. PATENT DOCUMENTS

| 4,558,119 A | * | 12/1985 | Yamashita et al. | 528/215 |
| 5,068,310 A | * | 11/1991 | Shaffer | 528/215 |
| 6,211,327 B1 | * | 4/2001 | F. M. Braat et al. | 528/217 |

FOREIGN PATENT DOCUMENTS

| JP | 57-177018 | 10/1985 |
| JP | 64-45427 | 2/1989 |
| JP | 8-12753 | 1/1996 |
| JP | 10-212350 | 8/1998 |
| JP | 11-100440 | 4/1999 |
| JP | 11-286542 | 10/1999 |

* cited by examiner

*Primary Examiner*—Duc Truong
(74) *Attorney, Agent, or Firm*—Dickstein, Shapiro, Morin & Oshinsky, LLP.

(57) ABSTRACT

A 2,6-dimethylphenol composition having an m-cresol content of from 15 to 700 ppm on a weight basis has effects of drastically improving polymerization activity and particularly, improving the color tone of polyphenylene ethers. Therefore, the composition makes it possible to provide a preparation process having improved productivity, and at the same time, provide polyphenylene ethers having good quality.

8 Claims, No Drawings

2,6-DIMETHYPHENOL COMPOSITION

TECHNICAL FIELD

The present invention relates to a 2,6-dimethylphenol composition, particularly to a monomer for the preparation of polyphenylene ether. The present invention also pertains to a process for the preparation of polyphenylene ether having highly improved polymerization activity and excellent color tone by using the monomer, and the polyphenylene ether obtained by the use of the monomer.

BACKGROUND ART

Polyphenylene ethers have been used widely as a material for products or parts in the fields of electrical or electronic fields, automotive fields, other industrial material fields, and food or packaging fields because they are excellent in workability and productivity, and can be produced as products or parts of a desired shape by melt injection or melt extrusion molding method.

A number of preparation processes of polyphenylene ethers have been proposed, for example, by Japanese Patent Publication No. Sho 36-18692 and U.S. Pat. Nos. 3,306,875, 3,344,116, and 3,432,466.

In these known publications, the monomer regarded as the most industrially important one is 2,6-dimethylphenol. By using this monomer, polyphenylene ethers having a very important role from the industrial viewpoint can be prepared.

In these many publications, 2,6-dimethylphenol has been used as a raw material without particular attention to impurities therein.

A technique paying attention to the impurities in 2,6-dimethylphenol is disclosed in an Example of Japanese Patent Laid-Open No. Hei 11-286542. Described specifically, a reduction in the content, in 2,6-dimethylphenol to be used for the polymerization, of alkylphenols other than 2,6-dimethylphenol to less than 0.3 wt. % has an effect of improving the activity. However, the above-described disclosure does not reveal whether or not high-molecular-weight polyphenylene ethers which are essentially necessary can be prepared, but only shows that an improvement in an initial oxygen absorption rate is observed, which is apparent to one of ordinary skill in the art. In addition, Japanese Patent Laid-Open No. Hei 11-286542 does not seem to include definite measures to improve the quality (particularly, color tone) of polyphenylene ethers.

Japanese Patent Laid-Open No. Sho 57-177018 describes a preparation process of polyphenylene ethers which comprises polymerizing, by continuous polymerization, 2,6-dimethylphenol containing, as impurities, 0.1 wt. % or less of m-cresol, 0.25 wt. % or less of o-cresol (component a), and 0.15 wt. % or less of p-cresol and/or 2,4,6-trimethylphenol (component b), the ratio (a/b) of components a and b falling within a range of from 0.5 to 25. As is apparent from the description, examples and comparative examples in this publication, all the impurities have a great influence on the molecular weight distribution of the resulting polyphenylene ethers and the precipitation ratio of dichloromethane. Hence, it is not clear from the disclosure of this publication which impurity will materially affect the above-mentioned molecular weight distribution or precipitation ratio. Furthermore, there is completely no information therein concerning the color tone possessed by the polyphenylene ethers.

It can be easily assumed from the conventional processes that, depending on the preparation process of 2,6-dimethylphenol to be used for polymerization, the amount of impurities differs and therefore, the polymerization activity or the molecular weight distribution of polyphenylene ethers cannot be controlled as desired. Consequently, it cannot be considered that the quality (particularly, color tone) of polyphenylene ethers has been fully examined.

DISCLOSURE OF THE INVENTION

An object of the present invention is to provide 2,6-dimethylphenol capable of improving polymerization activity, which property is of industrial significance, and providing polyphenylene ethers having excellent color tone.

With a view to achieving the above-described object, the present inventors made extensive investigations. As a result, it was surprisingly found that m-cresol in 2,6-dimethylphenol is a factor greatly influencing the color tone of polyphenylene ethers and inhibiting the polymerization activity, thus leading to the present invention.

The present invention therefore provides:

(1) A 2,6-dimethylphenol composition having an m-cresol content of from 15 ppm to 700 ppm based on the weight of 2,6-dimethylphenol.

(2) The 2,6-dimethylphenol composition of item (1) above, wherein the m-cresol content is from 15 ppm to 300 ppm.

(3) The 2,6-dimethylphenol composition of item (1) above, wherein the m-cresol content is from 15 ppm to 200 ppm.

(4) The 2,6-dimethylphenol composition of item (1) above, wherein the m-cresol content is from 15 ppm to 100 ppm.

(5) The 2,6-dimethylphenol composition of any one of items (1) to (4) above to be used as a raw material for flame retardants or sealants.

(6) The 2,6-dimethylphenol monomer composition of any one of items (1) to (4) above to be used for the preparation of polyphenylene ethers.

(7) A process for preparing a polyphenylene ether, which comprises subjecting a 2,6-dimethylphenol composition according to item (1), above, to oxidative polymerization using a catalyst and an oxygen-containing gas, wherein the catalyst comprises, as constituents thereof, a copper compound, a halogen compound and a diamine compound represented by the following formula (1):

wherein $R_1$, $R_2$, $R_3$ and $R_4$ each independently represents a hydrogen atom, a linear or branched $C_{1-6}$ alkyl group, with the proviso that they do not represent a hydrogen atom at the same time; and $R_5$ represents a linear or methyl-branched $C_{2-5}$ alkylene group.

(8) The process for preparing a polyphenylene ether according to item (7) above, wherein the catalyst further comprises, as the constituent thereof, at least one of a tertiary monoamine compound and a secondary monoamine compound.

(9) A polyphenylene ether obtained by oxidative polymerization of a 2,6-dimethylphenol composition according to item (1) above in the presence of a catalyst.

(10) The polyphenylene ether of item (9) above, which has an intrinsic viscosity [η], as measured at 30° C. in a chloroform solution, of 0.49 dl/g or less.

(11) A polyphenylene ether for retardants or sealants, which is obtained by oxidative polymerization of a 2,6-dimethylphenol composition according to item (1) above in the presence of a catalyst.

BEST MODE FOR CARRYING OUT THE INVENTION

The present invention will hereinafter be described specifically.

2,6-Dimethylphenol Composition

The 2,6-dimethylphenol composition of the present invention is useful as a monomer of polyphenylene ethers, a raw material for phosphate flame-retardants, or a raw material for sealants of electrical parts.

The 2,6-dimethylphenol composition of the present invention is 2,6-dimethylphenol containing m-cresol in an amount of from 15 ppm to 700 ppm on a weight basis. The m-cresol content is preferably from 15 ppm to 300 ppm, more preferably from 15 ppm to 200 ppm, most preferably from 15 ppm to 100 ppm. Control of the m-cresol content to fall within the above-described range is very effective for a marked improvement in the polymerization activity and particularly, the color tone of polyphenylene ethers.

For a further reduction of the m-cresol content in 2,6-dimethylphenol to less than 15 ppm, purification by the crystallization method is necessary. This method is, however, not preferred industrially, because it requires a tremendous equipment investment and running cost. In addition, effects brought about by reducing the m-cresol content to less than 15 ppm do not substantially exceed those of the present invention. Therefore, a reduction in the m-cresol amount to less than the above-described range is almost meaningless.

Examples of the other impurities which can be contained in 2,6-dimethylphenol include o-cresol, o-ethylphenol, p-cresol, 2,4-dimethylphenol, and 2,4,6-trimethylphenol. Contrary to expectation, however, the color tone of polyphenylene ethers is not affected by the amount of these impurities. They have a little influence on the polymerization activity, but it is not as intense as that of m-cresol. Therefore, a slight adjustment of the amount of the catalyst can remove such influence so that the cost increase necessitated thereby can be neglected. In the present invention, therefore, the amounts of alkylphenols other than m-cresol are not particular limited. This makes it possible to eliminate the work required to reduce the other impurities and to eliminate a cause of some disadvantages in the preparation of 2,6-dimethylphenol.

Polymerization Catalyst

The following polymerization catalysts are preferred for use in the present invention:

Catalysts comprising
(a) a copper compound, a halogen compound, and
(b) a diamine compound having a structure represented by the following formula (1):

(wherein, $R_1$, $R_2$, $R_3$ and $R_4$ each independently represents a hydrogen atom, a linear or branched $C_{1-6}$ alkyl group, with the proviso that they do not represent a hydrogen atom at the same time; and $R_5$ represents a linear or methyl-branched $C_{2-5}$ alkylene group).

Examples of the copper compound as a catalyst component (a) will next be described. As the copper compound, cuprous compounds, cupric compounds and mixtures thereof are preferred. The cupric compounds include cupric chloride, cupric bromide, cupric sulfate and cupric nitrate, while the cuprous compounds include cuprous chloride, cuprous bromide, cuprous sulfate and cuprous nitrate. Of these cuprous and cupric compounds, particularly preferred are cuprous chloride, cupric chloride, cuprous bromide and cupric bromide. These copper salts can be synthesized upon use from oxides, carbonates or hydroxides of copper, and halogens or acids corresponding thereto. Methods of mixing cuprous oxide and a hydrogen halide (or a solution of a hydrogen halide) are frequently used for the preparation of such copper salts.

Examples of the halogen compound include hydrogen chloride, hydrogen bromide, hydrogen iodide, sodium chloride, sodium bromide, sodium iodide, potassium chloride, potassium bromide, potassium iodide, tetramethylammonium chloride, tetramethylammonium bromide, tetramethylammonium iodide, tetraethylammonium chloride, tetraethylammonium bromide and tetraethylammonium iodide. These halogen compounds can be used as an aqueous solution or a solution in a proper solvent. These halogen compounds can be used, as the component, either singly or in combination with two or more thereof. Preferred halogen compounds are an aqueous solution of hydrogen chloride and an aqueous solution of hydrogen bromide.

Although no particular limitation is imposed on the amount of these compounds, they can be employed so that the amount of the halogen atom will be 2 moles or greater but not greater than 20 moles per mole of the copper atom. The amount of the copper atom will preferably be from 0.02 mole to 0.6 mole per 100 moles of the monomer.

Examples of the diamine compound as the catalytic component (b) will next be enumerated. Examples thereof include N,N,N',N'-tetramethylethylenediamine, N,N,N'-trimethylethylenediamine, N,N'-dimethylethylenediamine, N,N-dimethylethylenediamine, N-methylethylenediamine, N,N,N',N'-tetraethylethylenediamine, N,N,N'-triethylethylenediamine, N,N'-diethylethylenediamine, N,N-diethylethylenediamine, N-ethylethylenediamine, N,N-dimethyl-N'-ethylethylenediamine, N,N'-dimethyl-N-ethylethylenediamine, N-n-propylethylenediamine, N,N'-n-propylethylenediamine, N-i-propylethylenediamine, N,N'-i-propylethylenediamine, N-n-butylethylenediamine, N,N'-n-butylethylenediamine, N-i-butylethylenediamine, N,N'-i-butylethylenediamine, N-t-butylethylenediamine, N,N'-t-butylethylenediamine, N,N,N',N'-tetramethyl-1,3-diaminopropane, N,N,N'-trimethyl-1,3-diaminopropane, N,N'-dimethyl-1,3-diaminopropane, N-methyl-1,3-diaminopropane, N,N,N',N'-tetramethyl-1,3-diamino-1-methylpropane, N,N,N',N'-tetramethyl-1,3-diamino-2-methylpropane, N,N,N',N'-tetramethyl-1,4-diaminobutane, and N,N,N',N'-tetramethyl-1,5-diaminopentane. Preferred diamine compounds for use in the present invention are those in which the alkylene group that links the two nitrogen atoms has 2 or 3 carbon atoms. Although no particular limitation is imposed on the use amount of the diamine compound, it is usually employed in an amount ranging from 0.01 to 10 moles per 100 moles of the monomer.

To these catalyst components, the following components can be added as a preferred component in the present invention. Described specifically, tertiary monoamine compounds and secondary monoamine compounds can be added either singly or in combination with the catalyst components comprising the above-described copper compounds, halogen compounds and diamine compounds.

The term "tertiary monoamine compounds" means aliphatic tertiary amines including alicyclic tertiary amines. Examples thereof include, for example, trimethylamine, triethylamine, tripropylamine, tributylamine, triisobutylamine, dimethylethylamine, dimethylpropylamine, allyldiethylamine, dimethyl-n-butylamine, diethylisopropylamine and N-methylcyclohexylamine. These tertiary monoamines can be used either singly or in combination with at least two or more thereof. Although no particular limitation is imposed on the use amount, it is usually employed in an amount ranging from 0.1 to 10 moles per 100 moles of the monomer.

With regards to the secondary monoamine compounds, examples of secondary aliphatic amines include dimethylamine, diethylamine, di-n-propylamine, di-iso-propylamine, di-n-butylamine, di-iso-butylamine, di-tert-butylamine, dipentylamines, dihexylamines, dioctylamines, didecylamines, dibenzylamines, methylethylamine, methylpropylamine, methylbutylamine, and cyclohexylamine. Examples of secondary aromatic monoamines include N-phenylmethanolamine, N-phenylethanolamine, N-phenylpropanolamine, N-(m-methylphenyl)ethanolamine, N-(p-methylphenyl)methanolamine, N-(2',6'-dimethylphenyl)ethanolamine, N-(p-chlorophenyl)ethanolamine, N-ethylaniline, N-butylailine, N-methyl-2-methylaniline, N-methyl-2,6-dimethylaniline and diphenylamine. Secondary monoamine compounds are however not limited to the above-described ones. They can be used either singly or in combination of at least two or more thereof. Although no particular limitation is imposed on the use amount, it ranges from 0.05 mole to 15 moles per 100 moles of the monomer, with a range of from 0.1 to 10 moles being preferred.

The secondary monoamine compound and tertiary monoamine compound can be used either singly or in combination as constituents of the catalyst.

No limitation is imposed on the addition, to the polymerization catalyst of the present invention, of a surfactant conventionally known to have activity improving effects. For example, trioctylmethylammonium chloride known as the trade name of "Aliquat 336" or "Capriquat" can be used. Its use amount is preferably within a range not exceeding 0.1 wt. % based on the total amount of the whole reaction mixture after the addition of the monomer thereto.

Oxidative Polymerization

Although no particular limitation is imposed on the solvent to be used upon preparation of polyphenylene ethers insofar as it exhibits polymerization activity, typical examples thereof comprise one or more the following solvents. Examples include alcohols such as methanol, ethanol, n-propanol, iso-propanol, n-butanol, iso-butanol, sec-butanol, n-pentanol, n-hexanol and allyl alcohol, aromatic hydrocarbons such as benzene, toluene, xylene (including o-, m-, and p-isomers), ethylbenzene and styrene, halogenated hydrocarbons such as chloroform, methylene chloride, 1,2-dichloroethane, chlorobenzene and dichlorobenzene, nitro compounds such as nitrobenzene, aliphatic hydrocarbons such as pentane, hexane, heptane, cyclohexane and cycloheptane, esters such as ethyl acetate and ethyl formate, ethers such as tetrahydrofuran and diethyl ether, and dimethylsulfoxide. Of these, alcohols having 6 or less carbon atoms, xylene and toluene are preferred.

No particular limitation is imposed on the polymerization manner. By selecting a ratio of a good solvent to a poor solvent for a polyphenylene ether which is a polymer obtained by the oxidative polymerization of 2,6-dimethylphenol, polymerization can become solution polymerization, or precipitation polymerization in which the polymer is precipitated as particles in a reaction solvent with the progress of the reaction.

According to the present invention, any of the continuous polymerization, solution polymerization and precipitation polymerization methods can be applied.

In a polymerization reaction system, it is possible to add a hydroxide of an alkali metal, a hydroxide of an alkaline earth metal, an alkoxide of an alkali metal, a neutral salt such as magnesium sulfate, zeolite or the like The polymerization reaction temperature is set within a range of from 0 to 80° C., preferably from 10 to 70° C., because the reaction does not proceed smoothly if the temperature is too low, while the selectivity of reaction can be reduced if the temperature is too high.

As for the oxygen to be used for the oxidative polymerization in the present invention, a mixture of oxygen with an inert gas such as nitrogen mixed at a desired ratio, air or the like as well as pure oxygen can be used. With regards to the pressure in the system during the polymerization reaction, normal pressure is sufficient, but the reaction can be effected under reduced pressure or increased pressure as needed.

There is no particular limitation imposed on the post-treatment method after completion of the polymerization reaction. Any known treatment methods can be adopted. For example, the polyphenylene ether can be collected by a simple operation of adding an acid such as hydrochloric acid or acetic acid, ethylenediaminetetraacetic acid (EDTA) or salt thereof, or nitrilotriacetic acid or salt thereof to the reaction mixture to deactivate the catalyst, separating the resulting polymer from the mixture, washing it with a solvent, such as methanol, which does not dissolve the resulting polymer therein, and then drying.

Polyphenylene Ether

The polyphenylene ethers thus obtained are also embraced in the scope of the present invention. In general, polyphenylene ethers have excellent flame retardancy and electrical properties. The polyphenylene ethers obtained according to the present invention have, in addition to the above, excellent color tone so that they are useful as an additive such as flame retardant improver for imparting another substance with flame retardancy, or as an additive for sealants which are required to have a low dielectric constant, low dielectric loss, or the like. The polyphenylene ethers obtained by the process of the present invention are preferably employed for such purposes. In particular, polyphenylene ethers having an intrinsic viscosity [η] of 0.49 dl/g or less as measured at 30° C. in a chloroform solution are preferred.

The polyphenylene ethers according to the present invention have excellent color tone so that they can be advantageously applied to various thermoplastic resin compositions, thermosetting resins and the like. Examples of the use with a thermoplastic resin include, for example, compositions with a polystyrene resin (including rubber-reinforced polystyrene, AS resin, ABS resin and the like), polyamide resin, polyolefin resin, polyester resin, liquid crystal resin, thermoplastic elastomer or the like, while examples of the use with the thermosetting resin include, for example, compositions with an epoxy, unsaturated polyester, polyurethane, crosslinked aryl, bismaleimide, phenolic resin or the like. The thermoplastic resins and thermosetting resins are however not limited to these examples.

When a composition is prepared using the polyphenylene ether obtained by the present invention, additives other than the above-described ones can be incorporated. Examples thereof include plasticizers, stabilizers, modifiers, ultraviolet absorbers, flame retardants, coloring agents, mold release agents, fibrous reinforcing materials such as glass fibers and carbon fibers, and fillers such as glass beads, calcium carbonate and talc. Examples of the stabilizers or modifiers include, but not limited to, phosphites, hindered phenols, sulfur-containing antioxidants, alkanolamines, acid amides, metal salts of dithiocarbamic acid, inorganic sulfides, metal oxides, carboxylic anhydrides, dienophile compounds such as styrene and stearyl acrylate, and epoxy-containing compounds. These additives can be used either singly or in combination.

Components constituting the composition containing the polyphenylene ether of the present invention can be mixed in any manner. For example, a solution blending and deaeration method, extruder, heating roller, Banbury mixer, kneader, Henschel mixer or the like can be used.

EXAMPLES

The present invention will be described in greater detail with reference to the following Examples, but the invention should not be construed as being limited thereto.

(1) Evaluation Method of Activity

During the polymerization, sampling is carried out. After addition of methanol acidified with hydrochloric acid to the obtained sample, the mixture is filtered, followed by washing with methanol in repetition. The wet polyphenylene ether thus obtained is dried at 145° C. to obtain a dry polyphenylene ether. The reduced viscosity ($\eta$ sp/c) of the resulting polyphenylene ether in the form of a 0.5 g/dl chloroform solution is measured at 30° C. by using an Ubbelohde viscometer. The unit is dl/g. Against the polymerization time, the $\eta$ sp/c thus obtained is plotted and time to reach the desired $\eta$ sp/c is determined. This is designated as a necessary time and used as an index of activity. The desired $\eta$ sp/c varies depending on the physical properties of the target polyphenylene ether. In all the Examples of the present invention, however, the desired reduced viscosity is set equal to 0.70 dl/g.

(2) Measuring Method of the Color Tone (Color Index) of Polyphenylene Ethers

A reaction mixture of a polyphenylene ether prepared by polymerization was treated as described below and a product of the polyphenylene ether was obtained. When the reaction mixture of the polyphenylene ether after polymerization was in solution form, it was treated in accordance with the method as described in Japanese Patent Publication Sho. 61-20576. When the reaction mixture was in slurry form, it was treated in accordance with the method as described in Japanese Patent Laid-Open No. Hei 7-278293.

A 10 ml chloroform solution of 0.5 g of the polyphenylene ether thus purified was prepared and the absorbance (an absorbance measuring cell having a cell length of 1 cm was used) of the solution at 480 nm was measured using a UV-vis absorption spectrometer ("UV-3210", product of Hitachi). The absorbance thus obtained was divided by the concentration (0.05 g/ml) and the quotient is defined as a color index. A lower color index means that the color tone of the polyphenylene ether is better.

(3) Preparation of Pure 2,6-dimethylphenol

In order to show the advantage of the present invention clearly, it is necessary to compare 2,6-dimethylphenols which have different amount of the other alkylphenols therein. Comparison was therefore made by preparing an almost pure 2,6-dimethylphenol and a mixture of this 2,6-dimethylphenol with the other alkylphenols added as needed. The following is the process of obtaining the pure 2,6-dimethylphenol.

In a 200-L jacketed tank, 30 kg of impurity-containing 2,6-dimethylphenol obtained by a known process and 50 L of hexane were charged and continuously stirred while being heated to 40° C. by introducing a heating medium into the jacket. After the 2,6-dimethylphenol was dissolved completely, a cooling medium was introduced into the jacket to cool it to 0° C. Several hours later, the crystals of 2,6-dimethylphenol were precipitated in the tank so that they were collected by filtration. The same procedure was repeated using the crystals of 2,6-dimethylphenol thus obtained. By gas chromatography, 2,6-dimethylphenol thus obtained was analyzed. After 1.5000 g of the crystals of 2,6-dimethylphenol obtained by the above-described purifying operation was weighed precisely and put into a 10-ml measuring flask, methanol was added thereto. After the crystals were dissolved completely therein, the total volume was adjusted to 10 ml with addition of methanol, which was used as a measuring sample. As an analyzer, column, and carrier gas of gas chromatography, "GC-14BPTF" of Shimadzu Co., "DB-FFAP" (ID=0.25 mm, L=30 m, df=0.25 µm) of J&W, a helium gas were used, respectively. The temperature of a sample inlet was set at 300° C., while the temperature of the column was set at 150° C. Each component contained in the measuring sample was detected by a flame ionization detector kept at 250° C. A calibration curve was produced in advance based on the measuring result, under the same conditions, of a standard sample for each of the alkylphenols other than 2,6-dimethylphenol, and the composition of the other alkylphenols contained in the 2,6-dimethylphenol was determined. As a result, it was found that the total amount of the other alkylphenols contained in the purified 2,6-dimethylphenol was 10 ppm or less. The "other alkylphenols" referred to herein specifically include o-cresol, m-cresol, p-cresol, o-ethylphenol, 2,4-dimethylphenol and 2,4,6-trimethylphenol. The amount of m-cresol was not greater than a detection limit (0.2 ppm). By this operation, a pure 2,6-dimethylphenol was obtained. Polymerization in the below-described Examples or Comparative Examples was performed using the pure 2,6-dimethylphenol thus obtained by the above-described purifying operation.

Example 1

In a 50-L jacketed reactor equipped with, at the bottom of the reactor, a sparger for introducing an oxygen-containing gas, a stirring turbine blade and a baffle, and, in a vent gas line at the upper portion of the reactor, a reflux condenser having a decanter for separating the condensate attached at the bottom of the reflux condenser, 3.3497 g of cuprous oxide, 20.1484 g of a 47% aqueous solution of hydrogen bromide, 39.0655 g of di-n-butylamine, 99.0826 g of dimethyl-n-butylamine, 8.0692 g of N,N'-di-t-butylethylenediamine, 2.000 g of trioctylmethylammonium chloride and 14730.3 g of toluene were charged to prepare an initial feed solution. Under vigorous stirring, introduction of air was started at a rate of 28 L/min from the sparger. At the same time, addition of a solution, in 2498.0 g of toluene, of 2600 g of a monomer, which had been obtained by adding m-cresol to the purified 2,6-dimethylphenol to adjust the m-cresol content to 20 ppm, was started by a plunger pump at a rate that completes the charging in 30 minutes. The polymerization temperature was kept 40° C. by introducing a heating medium in the jacket. When the polymer solution became a little viscous, sampling was started little by little and the time necessary to reach the desired viscosity was determined by measuring the $\eta$ sp/c relative to the polymerization time. The results are shown in Table 1. The polymer mixture was in the solution form. The color index of the polyphenylene ether was measured after treating it in accordance with the above-described method as described in the section of the measuring method of the color tone (color index) of the polyphenylene ether. The results are also shown in Table 1.

Example 2

In the same manner as in Example 1 except that the purified 2,6-dimethylphenol was adjusted to contain 80 ppm of m-cresol, the reaction was effected. The necessary time and the color index of the polyphenylene ether are shown in Table 1.

Example 3

In the same manner as in Example 1 except that the purified 2,6-dimethylphenol was adjusted to contain 350 ppm of m-cresol, the reaction was effected. The necessary time and the color index of the polyphenylene ether are shown in Table 1.

Example 4

In the same manner as in Example 1 except that the purified 2,6-dimethylphenol was adjusted to contain 500 ppm of m-cresol, the reaction was effected. The necessary time and the color index of the polyphenylene ether are shown in Table 1.

Comparative Example 1

In the same manner as in Example 1 except that the purified 2,6-dimethylphenol was adjusted to contain 800 ppm of m-cresol, the reaction was effected. The necessary time and the color index of the polyphenylene ether are shown in Table 1.

Comparative Example 2

In the same manner as in Example 1 except that the purified 2,6-dimethylphenol was adjusted to contain 1500 ppm of m-cresol, the reaction was effected. The necessary time and the color index of the polyphenylene ether are shown in Table 1.

Comparative Example 3

In the same manner as in Example 1 except that the purified 2,6-dimethylphenol was used as is, the reaction was effected. The necessary time and the color index of the polyphenylene ether are shown in Table 1. The results in Comparative Example 3 were almost similar to those in Example 1, suggesting that the further removal of m-cresol by the crystallization method has substantially no meaning.

Example 5

In the same manner as in Example 1 except that the purified 2,6-dimethylphenol was adjusted to contain 80 ppm of m-cresol, 500 ppm of o-cresol, 500 ppm of p-cresol, 900 ppm of o-ethylphenol, 300 ppm of 2,4-dimethylphenol and 300 ppm of 6-trimethylphenol, the reaction was effected. The necessary time and color index of the polyphenylene ether are shown in Table 1.

Example 6

In a 30-L jacketed reactor equipped with a sparger for introducing an oxygen-containing gas, a stirring turbine blade and a baffle, each at the bottom of the reactor, and a reflux condenser in a vent gas line at the upper portion of the reactor, 3.7674 g of cupric chloride dihydrate, 16.1319 g of 35% hydrochloric acid, 25.4401 g of N-ethylaniline, 143.9057 g of N,N,N',N'-tetramethylpropanediamine, 1882 g of methanol, 1882 g of n-butanol and 5646.5 g of toluene were charged to prepare an initial feed solution. Under vigorous stirring, introduction of oxygen was started at a rate of 5.0 L/min from the sparger. At the same time, addition of a solution of 2700 g of the monomer, which had been prepared by adjusting the purified 2,6-dimethylphenol to contain 20 ppm of m-cresol, in a mixed solvent composed of 540 g of methanol, 540 g of n-butanol and 1620 g of toluene was started using a plunger pump at a rate that completes the charging of the whole amount in 30 minutes. The polymerization temperature was adjusted and kept at 40° C. by introducing a heating medium in the jacket. The polymer solution gradually became a slurry. When the polymer solution started to become a slurry, the sampling in portions was started and the necessary time was determined by measuring the η sp/c relative to the polymerization time. The results are shown in Table 1. The polymer mixture was in the slurry form. It was treated in accordance with the method as described above in the section of the measuring method of the color tone (color index) of polyphenylene ethers and the color index of the polyphenylene ether was measured. The results are also shown in Table 1.

Example 7

In the same manner as in Example 6 except that the purified 2,6-dimethylphenol was adjusted to contain 80 ppm of m-cresol, the reaction was effected. The necessary time and the color index of the polyphenylene ether are shown in Table 1.

Example 8

In the same manner as in Example 6 except that the purified 2,6-dimethylphenol was adjusted to contain 350 ppm of m-cresol, the reaction was effected. The necessary time and the color index of the polyphenylene ether are shown in Table 1.

Example 9

In the same manner as in Example 6 except that the purified 2,6-dimethylphenol was adjusted to contain 500 ppm of m-cresol, the reaction was effected. The necessary time and the color index of the polyphenylene ether are shown in Table 1.

Comparative Example 4

In the same manner as in Example 6 except that the purified 2,6-dimethylphenol was adjusted to contain 800 ppm of m-cresol, the reaction was effected. The necessary time and the color index of the polyphenylene ether are shown in Table 1.

Comparative Example 5

In the same manner as in Example 6 except that the purified 2,6-dimethylphenol was adjusted to contain 1500 ppm of m-cresol, the reaction was effected. The necessary time and the color index of the polyphenylene ether are shown in Table 1.

Comparative Example 6

In the same manner as in Example 6 except that the purified 2,6-dimethylphenol was used as is, the reaction was effected. The necessary time and the color index of the polyphenylene ether are shown in Table 1. The results in Comparative Example 6 were almost similar to those in Example 6, suggesting that the further removal of m-cresol by the crystallization method has substantially no meaning.

Example 10

In the same manner as in Example 6 except that the purified 2,6-dimethylphenol was adjusted to contain 80 ppm of m-cresol, 500 ppm of o-cresol, 500 ppm of p-cresol, 900 ppm of o-ethylphenol, 300 ppm of 2,4-dimethylphenol and 300 ppm of 2,4,6-trimethylphenol, the reaction was effected. The necessary time and color index of the polyphenylene ether are shown in Table 1.

Example 11

In the same manner as in Example 10 except that the addition of N-ethylaniline was omitted, the reaction was effected. The necessary time and the color index of the polyphenylene ether are shown in Table 1.

Comparative Example 7

In the same manner as in Example 5 except that the m-cresol content was adjusted to 800 ppm, the reaction was effected. The necessary time and the color index of the polyphenylene ether are shown in Table 1.

Comparative Example 8

In the same manner as in Example 10 except that the m-cresol content was adjusted to 800 ppm, the reaction was effected. The necessary time and the color index of the polyphenylene ether are shown in Table 1.

Example 12

In the same manner as in Example 5 except that the m-cresol content was adjusted to 200 ppm, the reaction was effected. The necessary time and the color index of the polyphenylene ether are shown in Table 1.

Example 13

In the same manner as in Example 10 except that the m-cresol content was adjusted to 200 ppm, the reaction was effected. The necessary time and the color index of the polyphenylene ether are shown in Table 1.

TABLE 1

Necessary time and color index in Examples and Comparative Examples

| | Catalyst employed | Kind and amount of the other alkylphenols added | | Necessary time (min) | Color index |
|---|---|---|---|---|---|
| Example 1 | A type | m-Cresol | 20 ppm | 108 | 0.21 |
| Example 2 | A type | m-Cresol | 80 ppm | 110 | 0.24 |
| Example 3 | A type | m-Cresol | 350 ppm | 118 | 0.39 |
| Example 4 | A type | m-Cresol | 500 ppm | 137 | 0.48 |
| Comp. Ex. 1 | A type | m-Cresol | 800 ppm | 168 | 0.60 |
| Comp. Ex. 2 | A type | m-Cresol | 1500 ppm | 189 | 0.77 |
| Comp. Ex. 3 | A type | Purified monomer was used as is | | 107 | 0.20 |
| Example 5 | A type | m-Cresol | 80 ppm | 119 | 0.24 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |
| Example 6 | B type | m-Cresol | 20 ppm | 122 | 0.30 |
| Example 7 | B type | m-Cresol | 80 ppm | 124 | 0.32 |
| Example 8 | B type | m-Cresol | 350 ppm | 128 | 0.34 |
| Example 9 | B type | m-Cresol | 500 ppm | 143 | 0.40 |
| Comp. Ex. 4 | B type | m-Cresol | 800 ppm | 183 | 0.59 |
| Comp. Ex. 5 | B type | m-Cresol | 1500 ppm | 215 | 0.80 |
| Comp. Ex. 6 | B type | Purified monomer was used as is | | 123 | 0.29 |
| Example 10 | B type | m-Cresol | 80 ppm | 130 | 0.31 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |
| Example 11 | C type | m-Cresol | 80 ppm | 139 | 0.39 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |
| Comp. Ex. 7 | A type | m-Cresol | 800 ppm | 171 | 0.61 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |
| Comp. Ex. 8 | B type | m-Cresol | 800 ppm | 188 | 0.62 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |
| Example 12 | A type | m-Cresol | 200 ppm | 124 | 0.24 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |

TABLE 1-continued

Necessary time and color index in Examples and Comparative Examples

| | Catalyst employed | Kind and amount of the other alkylphenols added | | Necessary time (min) | Color index |
|---|---|---|---|---|---|
| Example 13 | B type | m-Cresol | 200 ppm | 127 | 0.32 |
| | | o-Cresol | 500 ppm | | |
| | | p-Cresol | 500 ppm | | |
| | | o-Ethylphenol | 900 ppm | | |
| | | 2,4-Dimethylphenol | 300 ppm | | |
| | | 2,4,6-Trimethylphenol | 300 ppm | | |

In Table 1, the catalyst used in Examples 1 to 5, Example 12, Comparative Examples 1 to 3, and Comparative Example 7 was expressed as A type, the catalyst used in Examples 6 to 10, Example 13, Comparative Examples 4 to 6 and Comparative Example 8 was expressed as B type, and the catalyst used in Example 11 was expressed as C type.

The present invention has been described in detail and with reference to specific embodiments thereof. It will be apparent to one skilled in the art that various changes and modifications can be made therein without departing from the spirit and scope thereof.

The present application is based on Japanese Patent Application (Japanese Patent Application No. 2001-239820) filed on Aug. 7, 2001 and the content thereof is incorporated herein by reference.

INDUSTRIAL APPLICABILITY

In the present invention, by adjusting the m-cresol content in 2,6-dimethylphenol to a specific amount, the activity shows a significant improvement and particularly, the effects of improving the color tone of polyphenylene ethers become marked. This makes it possible to provide a preparation process of a polyphenylene ether with an improved productivity and at the same time, to provide a polyphenylene ether with good quality.

The invention claimed is:

1. A process for preparing a polyphenylene ether, which comprises subjecting a 2,6-dimethylphenol composition having an m-cresol content of from 15 ppm to 700 ppm based on the weight of 2,6-dimethylphenol to oxidative polymerization using a catalyst and an oxygen-containing gas, wherein the catalyst comprises, as constituents thereof, a copper compound, a halogen compound and a diamine compound represented by the following formula (1):

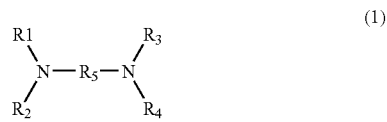

(1)

wherein $R_1$, $R_2$, $R_3$ and $R_4$ each independently represents a hydrogen atom, a linear or branched $C_{1-6}$ alkyl group, with the proviso that they do not represent a hydrogen atom at the same time; and $R_5$ represents a linear or methyl-branched $C_{2-5}$ alkylene group.

2. The process for preparing a polyphenylene ether according to claim 1, wherein the catalyst further comprises, as a constituent thereof, at least one of a tertiary monoamine compound and a secondary monoamine compound.

3. A polyphenylene ether obtained by the process as claimed in claim 1.

4. The polyphenylene ether of claim 3, which has an intrinsic viscosity [η], as measured at 30° C. in a chloroform solution, of 0.49 dl/g or less.

5. The process of claim 1, wherein the m-cresol content is from 15 ppm to 300 ppm.

6. The process of claim 1, wherein the m-cresol content is from 15 ppm to 200 ppm.

7. The process of claim 1, wherein the m-cresol content is from 15 ppm to 100 ppm.

8. The process of claim 1, wherein the oxidative polymerization is solution polymerization.

* * * * *